United States Patent [19]

Kubota et al.

[11] Patent Number: 5,116,973
[45] Date of Patent: May 26, 1992

[54] CAPROLACTAM SILANE COMPOUND AND A METHOD OF MANUFACTURING THE SAME

[75] Inventors: Tohru Kubota; Toshinobu Ishihara; Mikio Endo, all of Joetsu, Japan

[73] Assignee: Shin-Etsu Chemical Co., Ltd., Tokyo, Japan

[21] Appl. No.: 564,093

[22] Filed: Aug. 8, 1990

[30] Foreign Application Priority Data

Aug. 15, 1989 [JP] Japan .................................. 1-210400

[51] Int. Cl.$^5$ .......................... C07F 7/10; C07F 7/18; C07B 47/00
[52] U.S. Cl. ...................................................... 540/487
[58] Field of Search ......................................... 540/487

[56] References Cited

U.S. PATENT DOCUMENTS 2,876,234  3/1959  Hurwitz .............................. 540/487
3,780,025  12/1973 Thompson ........................... 540/487

FOREIGN PATENT DOCUMENTS 726099  4/1980  U.S.S.R. ................................ 540/487

OTHER PUBLICATIONS

Arkles, *Chemtech*, 13, pp. 542-555 (1983).

Primary Examiner—Mark L. Berch
Attorney, Agent, or Firm—Oblon, Spivak, McClelland, Maier & Neustadt

[57] ABSTRACT

A silane compound having the following formula, wherein $R^1$ and $R^2$ are each monovalent hydrocarbon radicals having 1 to 4 carbon atoms and n is an integer of 0, 1 or 2:

$$O=CCH_2CH_2CH_2CH_2CH_2N-CH_2CH_2CH_2SiR_n^1(OR^2)_{3-n}$$

which is manufactured by reacting 1-allyl-ε-caprolactam of the following formula:

$$O=CCH_2CH_2CH_2CH_2CH_2N-CH_2CH=CH_2$$

with a hydrogen silane of the following formula:

$$HSiR^1_n(OR^2)_{3-n}$$

in the presence of a platinum-containing catalyst. The silane compound is useful as a surface treatment agent for imparting a moisture-repelling property to the surface of various materials.

3 Claims, No Drawings

CAPROLACTAM SILANE COMPOUND AND A METHOD OF MANUFACTURING THE SAME

BACKGROUND OF THE INVENTION

1. Field of the Invention

The present invention relates to a silane compound which is useful as a surface treatment agent for imparting a moisture-repelling (anti-clouding) characteristic to the surface of various materials.

2. Description of the Background

Alkoxyl silane compounds having functional organic radicals are widely used to fix functional organic radicals to the surfaces of various foundation materials to thereby impart various characteristics to the foundation. For example, $CH_3(CH_2)_{17}Si(OCH_3)_3$ is effective to impart a hydrophobic characteristic to the surfaces of inorganic materials, and is, thus, used as an agent for treating the carriers of liquid and gas chromatographs. Being capable of creating a low energy surface over foundation materials, $CF_3(CF_2)_7CH_2CH_2Si(OCH_3)_3$ is used as a water- and oil-repelling agent and a releasing agent.

A need continues to exist, however, for silane compounds which exhibits a moisture-repelling (anti-clouding) characteristic to the surfaces of various materials.

SUMMARY OF THE INVENTION

Accordingly, it is an object of the present invention to provide a silane compound which exhibits a moisture-repelling (anti-clouding) characteristic to the surface of various materials.

It is also an object of this invention to provide a method of manufacturing the present silane compound.

The above objects and others which will become more apparent in view of the following are provided by a silane compound having the formula:

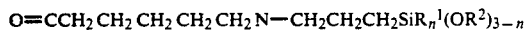

wherein $R^1$ and $R^2$ are monovalent hydrocarbon radicals having 1-4 carbon atoms and n is an integer of 0, 1 or 2.

DETAILED DESCRIPTION OF THE PREFERRED EMBODIMENTS

The present invention provides silane compounds, particularly a 3-(2-oxo-1-perhydroazepinyl) propyl silane compound, having the formula:

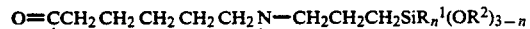

wherein $R^1$ and $R^2$ are monovalent hydrocarbon radicals having 1 to 4 carbon atoms and n is an integer of 0, 1 or 2.

The present invention also provides a method for preparing the present 3-(2-oxo-1-perhydroazepinyl) propyl silane compounds in high yield. In accordance therewith, 1-allyl-ε-caprolactam and a hydrogen silane are reacted in the presence of a catalyst. In particular, this method entails the hydrosilation of 1-allyl-ε-caprolactam of the formula:

with a hydrogen silane of the formula:

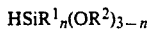

wherein $R^1$ and $R^2$ are monovalent hydrocarbon radicals having 1 to 4 carbon atoms and n is an integer of 0, 1 and 2, in the presence of a catalyst.

Generally, and as noted, the 3-(2-oxo-1-perhydroazepinyl) propyl silane compounds have the formula:

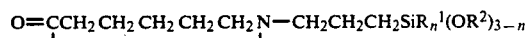

In this formula, $R^1$ and $R^2$ may each be a hydrocarbon radical having 1 to 4 carbon atoms such as methyl, ethyl, propyl, isopropyl, and butyl. The subscript n is any integer from 0 to 2. Examples of such silane compounds include 3-(2-oxo-1-perhydroazepinyl)propyltrimethoxyl silane; 3-(2-oxo-1-perhydroazepinyl)propylmethyldimethoxyl silane; 3-(2-oxo-1-perhydroazepinyl)propylmethyldiethoxyl silane; 3-(2-oxo-1-perhydroazepinyl)propylethyldiethoxyl silane; and 3-(2-oxo-1-perhydroazepinyl)propyldimethylbutoxyl silane.

These silane compounds are obtained at high yields through the present manufacturing method hereinafter described.

According to the method of the present invention, 1-allyl-ε-caprolactam of the following formula:

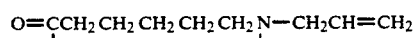

and a hydrogen silane of the following formula:

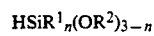

wherein $R^1$, $R^2$, and n are the same as defined above, are allowed to undergo hydrosilation in the presence of a catalyst.

The hydrogen silane used in the present method can be an alkoxyl silane such as trimethoxyl silane, methyldiethoxyl silane, ethyldiethoxyl silane, and dimethylbutoxyl silane; and the preferable dosage of the hydrogen silane is 1 to 1.5 times as much as the stoichiometrically equivalent amount of 1-allyl-ε-caprolactam.

The catalyst used in the method may be any known platinum-containing catalyst conventionally utilized in addition reactions. The amount used is preferably 10 to 500 ppm based on the amount of 1-allyl-ε-caprolactam used.

It is preferred that the hydrosilation is conducted in a reactor equipped with a stirrer, a thermometer, a reflux condenser, and a dropping funnel. It is also preferred that the reaction is conducted by dripping hydrogen silane into the reaction mixture which is maintained at a temperature of from 50° to 150° C.

In accordance with the present invention, it has also been found that the silane compound of the invention can also be obtained using a different method wherein a halosilane is utilized. In this alternative method, 1-allyl-ε-caprolactam having the following formula:

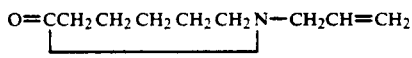

is allowed to undergo hydrosilation by reacting with a halosilane represented by the following formula:

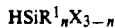

wherein $R^1$ and n are the same as defined above, and X is a halogen atom; in the presence of a catalyst; and then the reaction product is reacted with an alcohol having the following formula:

$R^2OH$ wherein $R^2$ is the same as defined above.

The halosilane used in this alternative method may be a chlorosilane such as trichlorosilane, methyldichlorosilane, butyldichlorosilane, and dimethylchlorosilane. It is preferred that the amount of the halosilane used is 1 to 1.5 times as much as the stoichiometrically equivalent amount of 1-allyl-ε-caprolactam.

As with the first disclosed method, this alternative method may also utilize a platinum-containing catalyst to promote the hydrosilation, and the amount used is preferably 10 to 500 ppm based on the amount of 1-allyl-ε-caprolactam used.

As with the first method, this hydrosilation is preferably carried out in a reactor equipped with a stirrer, a thermometer, a reflux condenser, and a dropping funnel. It is also preferred that this reaction is conducted by dripping halosilane in the reaction mixture which is maintained at a temperature of from 50° to 150° C.

According to this alternative method, the reaction product obtained from this hydrosilation is 3-(2-oxo-1-perhydroazepinyl)propyl halogenosilane represented generally by the following formula:

wherein $R^1$, X, and n are the same as defined above.

Then, by dripping an alcohol represented by the following formula into this halogenosilane, which is kept stirred, the silane compounds of the invention are obtained:

wherein $R^2$ is the same as defined above.

This alcohol may be methanol, ethanol, propanol, isopropanol, butanol, and the like; and the preferable amount of the alcohol used is 1 to 1.5 times as much as the stoichiometrically equivalent amount of the halogen atom in the halogenosilane.

In this manufacturing method, it is recommended that, after all the hydrogen silane is dripped and the reaction is completed, a tertiary amine, such as, for example, trimethyl amine and N,N-dimethyl aniline, as well as an aprotic solvent, such as, for example, toluene, xylene, hexane, and tetrahydrofuran, be added to the mixture prior to the addition of the alcohol.

When applied to surfaces of various substrate materials, the silane compounds of the present invention impart to the surfaces a semipermanent moisture-repelling characteristic to thereby prevent the surfaces from clouding. Especially when the surface is that of a transparent glass or similar material, the surface is not only rendered adamantly non-clouding but also protected by the layer of the compounds. The present compounds are also effective as coupling agents which improves the miscibility and adhesiveness between an inorganic material such as silica, glass fiber, and asbestos, and an organic high polymer such as polyamide resin and epoxy resin. Furthermore, since these silane compounds contain a 2-oxo-1-perhydroazepinyl group, which is a cyclic amide group, they can be utilized as reactants for copolymerization to obtain nylons, and in this way it is possible to improve the qualities of nylons especially with respect to heat resistance and strength.

The present invention will now be further explained by reference to certain examples which are provided solely for purposes of illustration and which are not intended to be limitative.

EXAMPLE 1

Preparation of 1-allyl-ε-caprolactam

In a 5 l. glass flask equipped with a stirrer, a fractionating column, a thermometer and a dropping funnel, 108.0 g (2.0 mol) of sodium methoxide and 1.5 l. of toluene were placed. ε-caprolactam in an amount of 226.3 g. (2.0 mol) had been dissolved in 0.5 l. of toluene, and this solution was added to the mixture in the flask by means of the dropping funnel at room temperature. The methanol produced was completely removed by distillation by means of the fractionating column. Bu₄NCl in an amount of 2.8 g. (10 millimol), as a phase transfer catalyst, was added to the residual mixture, to which thereafter was added 242.0 g. (2.0 mol) of allyl bromide through the dropping funnel at a temperature of 60°-70° C. whereby the mixture underwent reaction. After the reaction was completed, water was added to thereby dissolve the salt produced, and the organic layer was separated and distilled. The fraction corresponding to 95°-100° C./3 mmHg was separated and 219.7 g. of 1-allyl-ε-caprolactam was obtained. The yield was 71.7%.

EXAMPLE 2

Synthesis of 3-(2-oxo-1-perhydroazepinyl) propyltrimethoxyl silane

In a 300 ml. glass flask equipped with a stirrer, a thermometer, a reflux condenser and a dropping funnel, 76.6 g. (0.5 mol) of 1-allyl-ε-caprolactam and 0.3 g. of 4% isopropyl alcohol solution of H₂PtCl₆ were placed, and 61.1 g. (0.5 mol) of trimethoxyl silane was dripped through the dropping funnel in one hour at a temperature of 100° to 110° C., and the reaction mixture was let to ripen for one hour at 100° C. After the reaction, the mixture was distilled and 97.6 g of a chemical compound having a melting point of 149°-153° C. at 2 mmHg was separated. The results of analyses by mass spectrum (MS), nuclear magnetic resonance (NMR) spectrum, and infrared (IR) absorption spectrum of this compound, described hereinbelow, confirmed that this compound is of the following chemical formula:

The yield was 70.9%.

(1) Mass spectrum (electron impact-magnetic field type) m/z; 98 (standard peak), 121, 126, 228, 243, 275 (molecular weight peak)

(2) 1H-NMR spectrum: Assignment of spectrum to chemical structural formula:

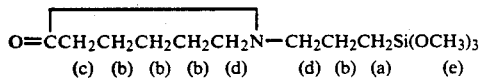

Chemical shift (TMS Standard) δ ppm; on the basis that CHCl$_3$ is observed at 7.26 ppm: (a) 0.46; (b) ca.1.5; (c) 2.35; (d) 3.19; (e) 3.41.

(3) 13C-NMR spectrum: Assignment of spectrum to chemical structural formula:

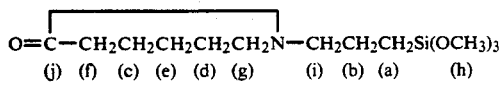

Chemical shift δ ppm; on the basis that CDCl$_3$ is observed at 77 ppm: (a) 6.1; (b) 20.9; (c) 23.2; (d) 28.4; (e) 29.7; (f) 37.0; (g) 49.2; (h) 50.2; (i) 50.4; (j) 175.2.

(4) Infrared absorption spectrum; cm$^{-1}$: 2940, 2840, 1645, 1490, 1450, 1430, 1375, 1360, 1295, 1265, 1240, 1230, 1205, 1090, 980, 815.

EXAMPLE 3

Synthesis of 3-(2-oxo-1-perhydroazepinyl) propylmethyldiethoxyl silane

Except that 67.1 g. (0.5 mol) of methyldiethoxyl silane was used in place of the 61.1 g. (0.5 mol) of trimethoxyl silane, the same procedure was observed as in Example 2, and 116.6 g. of a compound having a boiling point of 153°-155° C. at 3 mmHg was obtained. The results of analyses by mass spectrum (MS), nuclear magnetic resonance (NMR) spectrum, and infrared (IR) absorption spectrum of this compound, described hereinbelow, confirmed that this compound is of the following chemical formula:

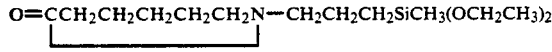

The yield was 81.1%.

(1) Mass spectrum (electron impact-magnetic field type) m/z; 98, 126, 133 (standard peak), 258, 272, 287 (molecular weight peak)

(2) 1H-NMR spectrum: Assignment of spectrum to chemical structural formula:

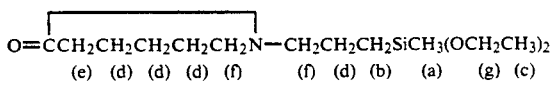

Chemical shift (TMS Standard) δ ppm; on the basis that CHCl$_3$ is observed at 7.26 ppm: (a) −0.01; (b) 0.45; (c) 1.09; (d) ca. 1.5; (e) 2.38; (f) 3.22; (g) 3.62

(3) 13C-NMR spectrum: Assignment of spectrum to chemical structural formula:

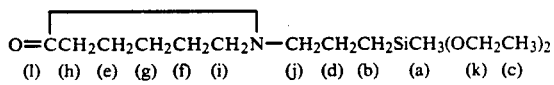

Chemical shift δ ppm; on the basis that CDCl$_3$ is observed at 77 ppm: (a) −5.2; (b) 10.8; (c) 18.1; (d) 21.2; (e) 23.2; (f) 28.4; (g) 29.7; (h) 37.1; (i) 49.3; (j) 50.7; (k) 57.8; (l) 175.2.

(4) Infrared absorption spectrum; cm$^{-1}$: 2970, 2920, 1645, 1490, 1450, 1430, 1400, 1375, 1360, 1290, 1260, 1215, 1205, 1170, 1110, 1080, 980, 955, 820.

Having described the present invention, it will be apparent to one of ordinary skill in the art that many changes and modifications may be made to the above-described embodiments without departing from the spirit and scope of the present invention.

What is claimed as new and desired to be secured by letters patent of the United States is:

1. A silane compound having the following formula, wherein R$^1$ and R$^2$ are each a monovalent hydrocarbon radical having 1 to 4 carbon atoms and n is an integer of 0, 1 or 2:

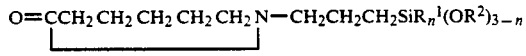

2. The silane compound as claimed in claim 1, wherein each of R$^1$ and R$^2$ are independently methyl, ethyl, propyl, isopropyl and butyl.

3. The silane compound as claimed in claim 1, which is selected from the group consisting of 3-(2-oxo-1-perhydroazepinyl)propyltrimethoxyl silane, 3-(2-oxo-1-perhydroazepinyl)propylmethyldimethoxyl silane; 3-(2-oxo-1-perhydroazepinyl)propylmethyldiethoxyl silane; 3-(2-oxo-1-perhydroazepinyl)propylethyldiethoxyl silane and 3-(2-oxo-1-perhydroazepinyl)propyldimethylbutoxyl silane.

* * * * *